(12) United States Patent
Winkel et al.

US007897190B2

(10) Patent No.: US 7,897,190 B2
(45) Date of Patent: Mar. 1, 2011

(54) FLAVOUR MODULATING SUBSTANCES

(75) Inventors: Chris Winkel, Bussum (NL); Harry Renes, Lelystad (NL)

(73) Assignee: Quest International Services B.V., Narrden (NL)

( * ) Notice: Subject to any disclaimer, the term of this patent is extended or adjusted under 35 U.S.C. 154(b) by 660 days.

(21) Appl. No.: 11/718,288

(22) PCT Filed: Oct. 6, 2005

(86) PCT No.: PCT/NL2005/000719
§ 371 (c)(1),
(2), (4) Date: Nov. 19, 2007

(87) PCT Pub. No.: WO2006/046853
PCT Pub. Date: May 4, 2006

(65) Prior Publication Data
US 2008/0206422 A1    Aug. 28, 2008

(30) Foreign Application Priority Data

Oct. 29, 2004 (EP) .................................... 04077980
Apr. 6, 2005 (WO) ................ PCT/NL2005/000258

(51) Int. Cl.
*A23L 2/56* (2006.01)
(52) U.S. Cl. ........................................................ 426/536
(58) Field of Classification Search ................... 426/536
See application file for complete search history.

(56) References Cited

U.S. PATENT DOCUMENTS

| 4,274,862 | A | 6/1981 | Kirino et al. | |
| 6,265,611 | B1 * | 7/2001 | Ley ............................. | 564/170 |
| 6,287,620 | B1 | 9/2001 | Van Den Ouweland et al. | |
| 2004/0072254 | A1 | 4/2004 | Callamaras et al. | |
| 2005/0013846 | A1 | 1/2005 | Pelan et al. | |

FOREIGN PATENT DOCUMENTS

| GB | 814570 | 6/1959 |
| GB | 2 396 414 A | 6/2004 |
| WO | WO 90/06689 | 6/1990 |
| WO | WO 97/04667 | 7/1996 |
| WO | WO 01 77292 A2 | 10/2001 |
| WO | WO 02/100192 A1 | 12/2002 |
| WO | WO 2004/055048 A2 | 7/2004 |
| WO | WO 2004/075633 A1 | 9/2004 |

OTHER PUBLICATIONS

Brauss, et al. "Altering the fat content affects flavor release in a model yogurt system." Journel of Agricultural Food Chemistry, 1999, 47, 2055-2059.*
Cliff, M., et al., "Descriptive analysis of oral pungency.", Journal of Sensory Studies, 1992, 279-290, 7, Food & Nutrition Press, Inc., Connecticut.
Dalton, P., et al., "The merging of the senses: integration of sub-threshold taste and smell.", Nature Neuroscience, May 2000, p. 431, vol. 3 No. 5, Nature America, Inc.
Suzuki, H., et al., "Improvement of the bitter taste of amino acids through the transpeptidation reaction of bacterial γ-glutamyltranspeptidase.", Journal of Agricultural and Food Chemistry, 2002, 313-318, 50 No. 2, American Chemical Society.
Pronin, A., et al., "Identification of ligands for two human bitter T2R receptors.", Chemical Senses, 2004, 583-593, vol. 29 No. 7, Oxford University Press.
Ueda, Y., et al., "Flavor characteristics of glutathione in raw and cooked foodstuffs.", Biosci. Biotech. Biochem., 1997, 1977-1980, 61.
Shima, K., et al., "Novel brothy taste modifier isolated from beef broth.", J. Agric. Food Chem., 1998, 1465-1468, 46, American Chemical Society.
Lindermann, B., "Receptors and transduction in taste.", Nature, Sep. 13, 2001, 219-225, vol. 413, Macmillan Magazines Ltd.
Breslin, P., "Interactions among salty, sour and bitter compounds.", Trends in Food Science & Technology, Dec. 1996, 7, 390-399, Elsevier Science Ltd.

* cited by examiner

*Primary Examiner* — C. Sayala
*Assistant Examiner* — Jenna A Watts
(74) *Attorney, Agent, or Firm* — Sughrue Mion, PLLC

(57) ABSTRACT

The present invention in a first aspect relates to novel flavour modulating substances according to formula (I) and/or edible salts thereof: R< SUP> 1< /SUP> —CR< SUP> 2< /SUP> (OR< SUP> 3< /SUP>) —CO—NR< SUP> 4< /SUP> —Y—X (I). It was found that substances represented by formula (I) can advantageously be used to impart desirable flavour, especially taste attributes to foodstuffs, beverages, and pharmaceutics they are incorporated in. In addition said substances are capable of modulating and complementing the sensory impact of other, flavour imparting, substances. Thus, the present flavour modulating substances are advantageously applied in flavour compositions, foodstuffs, beverages and pharmaceutics. Typical examples of flavour modulating substances according to the present invention include N-lactoyl tyramine, Nqgluconyl tyramine, N-lactoyl 4-hydroxyben zylamine, N-lactoyl vanillylamine and N-lactoyl-dopamine.

10 Claims, No Drawings

FLAVOUR MODULATING SUBSTANCES

FIELD OF THE INVENTION

The present invention concerns novel flavour modulating substances that may advantageously be applied in foodstuffs, beverages and pharmaceutics. The flavour modulating substances according to the invention are capable of modulating the impact of flavour imparting substances. The present invention also provides flavour compositions that can be used to confer a fuller and richer taste and/or aroma to foodstuffs, beverages and pharmaceutics. The present invention also encompasses the use of the aforementioned flavour modulating substances for improving the flavour of foodstuffs, beverages and pharmaceutics, as well as to foodstuffs, beverages and pharmaceutics containing these substances.

BACKGROUND OF THE INVENTION

The flavour of foodstuffs and beverages consists of two parts: the aroma and the taste. In general what is perceived through the olfactory epithelium in the nasal cavity is referred to as 'aroma', whereas the term 'taste' is generally used to describe the sensory impact that is perceived via the mouth, especially the tongue. The sense of taste provides the final analysis of food prior to ingestion thereof. Visual and olfactory signals already give a first indication but only after intake of the food into the mouth the final decision is made either to ingest or to reject the food. Sweet taste is usually a signal that the food is safe (nice) leading to ingestion of the food. The 'reactions' to salt and umami are really dependent on the strength of the signal. Bitter and sour are usually repulsive taste sensations, leading to rejection. Temperature is another measure by which the food is judged just as well as aching sensations like capsaicin (hot pepper) and certain chemicals (like carbon dioxide).

In short, this means that taste is a very crucial and very complex system. Until recently most flavour research was focused towards aroma. Especially the last years a series of publications relating to molecules with a (positive) contribution to the taste of foodstuffs has emerged.

Such research has been stimulated significantly by the fact that quite some receptors which are involved in the different taste sensations have been characterized by now (B. Lindemann; Nature 413, 219 (2001)).

Several screening systems have been described that make it possible to screen, in a short time, large series of molecules for their (modulating) effect on taste response (cf. WO04055048, GB2396414, WO0177292 and US2004/0072254).

It is remarkable that most research on these taste modulating molecules so far has been devoted to taste enhancement in savoury products. Several, mainly Japanese, publications describe umami molecules, i.e. alternatives to mono sodium glutamate (MSG) (H Suzuki et al, J Agric Food Chem 50, 313-318 (2002); K Shima et al, J Agric Food Chem 46, 1465-1468 (1998); Y Ueda et al, Biosc Biotech Biochem 61 1977 (1997)).

In EP 1291342, a 'general taste enhancer' is disclosed that was reported to be suitable for enhancing sweetness as well.

In patent applications WO9704667 and WO04075633 tripeptides and amino acid condensates with lactic acid and succinic acid are described that have both their own taste as well as some enhancing properties. Alpha keto acids are reported to give body and mouthfeel to foodstuffs they are added to (U.S. Pat. No. 6,287,620).

Chlorogenic acids are claimed to enhance sweetness and to reduce bitterness (WO02100192).

In sweet and beverage products, further examples of the importance of the gustative dimension of flavourings have been reported including bitterness, tingling and cooling-freshness.

Bitterness is an essential aspect of some food flavours, among which chocolate taste. Purine alkaloids, like theombromine and caffeine, as well as amino acids and peptides have been known for a long time as bitter compounds. In British patent no. GB 1420909 it is disclosed that the bitter flavour of cocoa can be reproduced using a combination of a purine alkaloid and an amino acid or an oligopeptide which 'produces a surpringly more natural simultaneously bitter and astringent flavour note than either of these types of substances alone'.

Quite a bit of work has been devoted to find bitter taste suppressors (A. N. Pronin et al, Chemical Senses 29, 583-593 (2004); EP1401500; P. A. Breslin, Trends in Food Science & Technology 7, 390-399 (1996)).

Menthol, an important constituent of peppermint oil, has a strong impact on flavoured products not only because of its mint smell but also because it imparts a cooling, fresh taste. Next to mint flavoured products, the use of menthol in other type of flavour to impart a cool taste has been suggested. US patent application no. US 2005/013846, for example, discloses how menthol and derivatives thereof can be used as flavouring in water continuous spreadable acidified food products to obtain table spreads exhibiting a fresh, cool taste impression.

Similarly, cinnamic aldehyde and eugenol, constituents of cinnamon oil, are used in flavouring composition for confectionary products, not only for their smell but also because they impart a warm and piquant-tingling taste. The oral pungency of cinnamic aldehyde was described as burning and tingling by Cliff M and Heymann H [Journal of Sensory Studies 7 (1992)279-290]. According to the same authors eugenol exhibits a long-lasting numbing effect. Cinnamon oil has been proposed as a taste improving flavouring. International patent application no. WO 90/06689 discloses that cinnamon oil, among other spice extracts, added to a minty flavour formulation, can be used to improve the long-lasting flavour of chewing-gum.

Another interesting aspect of taste is that it can have an impact on aroma. It was reported that people having artificially sweetened water in their mouth were significantly more sensitive to the smell of benzaldehyde than people having plain water in their mouth (P. Dalton et al, Nature Neurosci. 3, 431-432 (2000)).

The aim of the present invention is to provide new 'flavour modulating substances' that provide a positive contribution to the overall flavour impression of foodstuffs, beverages, and/or pharmaceutics they are incorporated in.

SUMMARY OF THE INVENTION

The present inventors have surprisingly found that flavour modulating substances represented by the following formula (I) and/or edible salts thereof can be used advantageously for modulating the flavour of foodstuffs, beverages and pharmaceutics:

$$R^1—CR^2(OR^3)—CO—NR^4—Y—X \quad (I)$$

The flavour improving substances according to the present invention can be applied advantageously to impart desirable flavour, especially taste, attributes to the aforementioned products. In addition, the present flavour improving substances are capable of modifying the taste and/or aroma impact of other flavour ingredients contained within these same products, thereby improving the overall flavour quality of these products.

A substance according to formula (I) wherein Y represents dimethyl-substituted methylene, X represents phenyl, $R^1$ represents $C_4$ alkyl $R^2$ and $R^4$ represent hydrogen and $R^3$ represents methyl has been described previously in U.S. Pat. No. 4,274,862, which document relates to herbicidal compositions and methods for controlling weeds. U.S. Pat. No. 4,274,862 does not in any way mention or refer to flavour characteristics of the substances disclosed therein.

Thus, the present invention relates to flavour modulating substances according to formula (I) and/or edible salts thereof, as well as to flavour compositions, foodstuffs, beverages and pharmaceutics, comprising one or more substances according to formula (I) and/or edible salts thereof.

Other aspects of the present invention relate to the use of the substances according to formula (I) and/or edible salts thereof for modulating, especially enhancing, the flavour of foodstuffs, beverages and pharmaceutics, and to a process for modulating the flavour of the latter products.

DETAILED DESCRIPTION OF THE INVENTION

The present invention in a first aspect relates to a flavour composition comprising at least 0.1 wt. % of one or more flavouring substances and between 0.001 and 80 wt. % of one or more flavour modulating substances according to formula (I) and/or edible salts thereof:

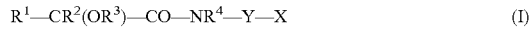

wherein:
Y represents a covalent bond, $C_1$-$C_5$ alkylene or $C_2$-$C_5$ alkenyl, each optionally substituted with 1-5 substituents selected from hydroxyl, $C_1$-$C_3$ alkoxyl and $C_1$-$C_3$ acyl;
X represents phenyl, substituted with one or more substituents selected from hydroxyl and $C_1$-$C_3$ alkoxyl, and optionally further substituted with one or more substituents selected from $C_1$-$C_3$ hydroxyalkyl
$R^1$ represents hydrogen; $C_1$-$C_8$ alkyl, $C_2$-$C_8$ alkenyl, $C_3$-$C_8$ cycloalkyl or $C_3$-$C_8$ cycloalkenyl, each optionally substituted with 1-8 substituents selected from hydroxyl, oxo, $C_1$-$C_3$ alkyl, $C_1$-$C_3$ alkoxyl, $C_1$-$C_3$ acyl, $C_2$-$C_3$ alkenyl-and $C_1$-$C_3$ carboxyl;
$R^2$ represents hydrogen; $C_1$-$C_8$ alkyl, $C_2$-$C_8$ alkenyl, $C_3$-$C_8$ cycloalkyl, or $C_3$-$C_8$ cycloalkenyl, each optionally substituted with 1-8 substituents selected from hydroxyl, $C_1$-$C_3$ alkyl, $C_2$-$C_3$ alkenyl and $C_1$-$C_3$ carboxyl;
$R^3$ represents hydrogen; or $C_1$-$C_3$ acyl or $C_1$-$C_3$ alkyl, each optionally substituted with 1-3 hydroxyl groups; and
$R^4$ represents hydrogen; $C_1$-$C_6$ alkyl, $C_2$-$C_6$ alkenyl, $C_1$-$C_3$ acyl, $C_3$-$C_6$ cycloalkyl, $C_3$-$C_6$ cycloalkenyl or $C_1$-$C_6$ acyl, each optionally substituted with 1-6 substituents selected from hydroxyl, $C_1$-$C_3$ alkyl and $C_2$-$C_3$ alkenyl.

The present inventors have found that the above-mentioned substances are very useful ingredients which, particularly in the presence of other flavour imparting substances, are capable of imparting highly appreciated taste sensations to the products in which they are incorporated, specifically a quite remarkable "roundness", "fullness", "substance", "fermented fish character" and/or "continuity". Because of this, the present flavour modulating substances can be employed to improve the taste (including "mouthfeel") of foodstuffs, beverages and pharmaceutics. In addition, it has been found that the flavour modulating substances according to the invention are capable of complementing and modifying the sensory impact of other, flavour imparting, substances contained in the aforementioned products.

The term "flavour modulating" as used herein refers to the capability of a composition or substance to alter the taste and/or aroma impact of other, flavour imparting, substances present within the same product, with the proviso that this change in taste and/or aroma impact is not caused by a flavour contribution of said substance per se, but instead that it mainly results from the combined effect of on the one hand the flavour modulating substance and on the other hand the other flavour imparting substances. The present substances combine the capability of modifying the taste of other flavour substances and a taste contribution of their own. The favorable impact of the present flavour modulating substances is believed to be the result of the combination of these two effects. Because the flavour modulating substances according to the invention are not particularly volatile, they do not produce a strong aroma impact, even though they do affect the aroma impact of other flavour imparting substances. Here the term "aroma" refers to the aspect of flavour that is perceived through the olfactory epithelium. Because of the low volatility of the present flavour modulating substances it is believed that the advantageous properties of these substances are somehow associated with the impact that these substances have on the sensory receptors located within the mouth.

A particularly preferred embodiment of the present invention related to flavour modulating substances according to formula (I) wherein Y represents a covalent bond or a linear $C_1$-$C_5$ alkylene or $C_2$-$C_5$ alkenyl, each optionally substituted with 1-5 substituents selected from hydroxyl, $C_1$-$C_3$ alkoxyl and $C_1$-$C_3$ acyl;

It was found that particularly satisfying results can be obtained with flavour modulating substances according to formula (I) wherein Y represents a $C_1$-$C_3$ alkylene or alkenyl, each optionally substituted with 1-3 substituents selected from hydroxyl and $C_1$-$C_2$ alkyl. More preferably, Y represents ethylene or methylene, optionally substituted with hydroxyl and/or methyl. Even more preferably, Y represents ethylene or methylene.

According to another preferred embodiment X represents hydroxyphenyl, optionally further substituted with 1 or 2 substituents selected from hydroxyl or methoxyl. Even more preferably X represents hydroxyphenyl, most preferably 4-hydroxyphenyl; dihydroxyphenyl, preferably 3,4-dihydroxyphenyl; trihydroxyphenyl, preferably 3,4,5-trihydroxyphenyl; or hydroxy-methoxyphenyl, preferably 4-hydroxy-3-methoxyphenyl.

According to another preferred embodiment, $R^1$ represents $C_2$-$C_6$ alkyl or $C_4$-$C_6$ cycloalkyl, wherein each carbon atom is substituted with a substituent independently selected from hydroxyl, oxo, carboxyl, $C_1$-$C_3$ alkoxyl and $C_1$-$C_3$ acyl. Even more preferably, $R^1$ represents $C_2$-$C_6$ alkyl, wherein each carbon atom is substituted with a single hydroxyl group. Most preferably, $R^1$ represents $C_3$-$C_5$ alkyl, wherein each carbon atom is substituted with a single hydroxyl group. Hence, according to this embodiment $R^1$—$CR^2(OR^3)$—CO— preferably represents the residue of an aldonic acid, more preferably a $C_5$ or $C_6$ aldonic acid.

Alternatively, in another preferred embodiment $R^1$ represents $C_1$-$C_4$ alkyl, more preferably $C_1$-$C_2$ alkyl, most preferably methyl.

In the aforementioned formula (I) $R^2$ preferably represents hydrogen or $C_1$-$C_4$ alkyl, most preferably hydrogen. Likewise, $R^3$ preferably represents hydrogen or $C_1$-$C_3$ alkyl, most preferably it represents hydrogen.

In formula (I), $R^4$ preferably represents hydrogen.

In a particularly preferred embodiment the present flavour modulating substances are selected from the group consisting of N-lactoyl tyramine, N-gluconyl-tyramine, N-lactoyl 4-hydroxybenzylamine, N-lactoyl vanillylamine, N-lactoyl-dopamine, edible salts thereof and mixtures thereof. Most preferably the flavour modulating substance is N-lactoyl tyramine.

According to a particularly preferred embodiment, the aforementioned flavour composition comprises at least 0.1 wt % of flavouring substances and one or more of the flavour modulating substances in an amount of at least at least 0.01 wt. %. Most preferably, the flavour composition contains at least 0.1 wt. % of the present flavour modulating substances. Preferably the amount of the present flavour modulating substances does not exceed 80 wt %, more preferably it does not exceed 40 wt. %. Here the term "flavouring substance" refers to any substance that is capable of imparting a detectable flavour impact, especially at a concentration below 0.1 wt. %, more preferably below 0.01 wt. %. In a preferred embodiment the flavour composition according to the invention comprises a flavouring substance in an amount of at least 0.5 wt. %, preferably at least 1 wt. %, based on the total weight of the composition.

Typically, in the present flavour composition, the flavour modulating substances and flavouring substances as defined herein before are employed in a weight ratio within the range of 10:1 to 1:100, preferably in a weight ratio of 5:1 to 1:50.

The flavour composition according to the present invention may suitably be prepared in the form of a liquid, a paste or a powder. In a particularly preferred embodiment the flavour composition is a free flowing powder.

Typical examples of flavour compositions according to the present invention include flavourings like fish flavourings, fish sauce flavourings, shrimp flavourings and fermented soy flavourings.

Another aspect of the present invention relates to a product selected from the group consisting of foodstuffs, beverages and pharmaceutics, said product comprising at least 0.1 ppm, more preferably at least 1 ppm, most preferably at least 3 ppm of one or more flavour modulating substances according to formula (I) and/or edible salts thereof. Typically, the aforementioned products will contain the flavour modulating substances in a concentration of not more than 1000 ppm, preferably of not more than 500 ppm.

Typical examples of foodstuffs according to the present invention include soups, sauces, stocks, bouillons, cheese products, dressings, seasonings, margarines, shortenings, bread, pastry, noodles, dairy products and beverages.

Yet another aspect the present invention relates to a process of modulating, especially improving, the flavour of a foodstuff, a beverage or a pharmaceutical product, comprising incorporating into said foodstuff beverage or pharmaceutical product one or more flavour modulating substances according to formula (I) and/or edible salts thereof, in an amount of at least 0.1 ppm, preferably of at lest 1 ppm, most preferably at least 3 ppm.

In yet another aspect, the present invention relates to flavour modulating substances according to formula (I) and/or edible salts thereof wherein Y represents a covalent bond, a linear $C_1$-$C_5$ alkylene or $C_2$-$C_5$ alkenyl, each optionally susbtituted with 1-5 substituents selected from hydroxyl, $C_1$-$C_3$ alkoxyl and $C_1$-$C_3$ acyl and wherein X, R1, R2, R3 and R4 have the same meaning as defined herein before. A preferred embodiment relates to flavour modulating substances according to formula (I) and/or edible salts thereof wherein Y represents ethylene or methylene and to compositions comprising them in the aforementioned amounts.

The flavour modulating substances according to formula (I) are suitably produced by reacting a primary or secondary amine with an α-hydroxyl carboxylate. Thus, yet another embodiment of the present invention relates to a process of producing a flavour modulating substance according to formula (I), comprising the step of reacting a substance according to formula (II) with an α-hydroxyl carboxylate or an α-hydroxyl carboxylate derivative according to formula (III) or a salt of said carboxylate or derivative.

$$HNR^4—Y—X \quad (II)$$

$$R^1—CR^2(OR^3)—COOR^5 \quad (III)$$

wherein X, Y, $R^1$, $R^2$, $R^3$ and $R^4$ have the same meaning as defined above in relation to formula (I); and wherein $R^5$ represents hydrogen or $C_1$-$C_3$ alkyl. The invention also encompasses reacting a substance according to formula (II) with a lactone that is formed by internal esterification of a substance according to formula (III) wherein $R^1$ and/or $R^2$ contain a hydroxyl group; The present invention, in another embodiment, encompasses flavour modulating compositions obtainable by the processes described above, flavouring compositions comprising these and the use thereof for improving the flavour of foodstuffs, beverages or pharmaceutics.

In still an alternative embodiment of the present invention a process for producing so-called 'process flavours' is provided, said process comprising heating a combination of a carbohydrate source and a nitrogen source in a continuous liquid phase containing at least 10 wt % of an α-hydroxycarboxylic acid component selected from the group of α-hydroxycarboxylic acids according to formula (III), salts thereof and derivatives thereof, wherein said combination of a carbohydrate source and a nitrogen source additionally comprises one or more substances according to formula (II) and/or salts thereof Most preferably the carbohydrate source comprises glucose or xylose the nitrogen source comprises amino acids, hydrolyzed proteins or yeast extracts, the substance according to formula (III) is selected from lactic acid and the substance according to formula (II) is selected from tyramine, dopamine, 4-hydroxybenzylamine, vanillylamine and salts thereof, most preferably tyramine. Process flavours obtained by said process will typically comprise one or more of the present flavour modulating substances. Thus another aspect of the invention relates to process flavours comprising 0.0001-0.01 wt %, preferably 0.0001-0.001 wt % of one or more substances according to formula I. In a particularly preferred embodiment the nitrogen source is provided by yeast extracts.

The invention is further illustrated by means of the following examples.

EXAMPLES

Example 1

Lactic acid (9 g) and tyramine (3 g ) were mixed and heated for 4 hrs at 120° C. The reaction mixture was cooled and washed with ethyl acetate. The residue (7 g) was dissolved in 25 g of water. NMR showed that at least 20% of the reaction mixture was N-lactoyl-tyramine.

Subsequently 12 g of maltodextrin (MD 10) and 6 g of salt were added and the slurry was spray-dried.

Example 2

Preparation of Pure N-lactoyl Tyramine 40 g of ethyl lactate and 10 g of tyramine were reacted at 120° C. for 4 hours. The reaction product was cooled and dissolved in 200 g water. The solution obtained was washed first with 200 ml of ethyl acetate and then with another 100 ml of ethyl acetate. The water phase was evaporated to dryness under vacuum at 70° C. 7.5 g of a very viscous liquid was obtained; analysis by LC-MS and NMR showed that it contained 60% of N-lactoyl tyramine.

This product was then purified using preparative liquid chromatography. The separation was carried out on two 100× 20 mm ID 5 μm Atlantis dC18 columns (Waters, Milford, Mass., USA) in tandem. Gradient elution was carried out with liChrosolv water (A) and liChrosolv acetonitrile (B) (Merck, Darmstadt, Germany) as follows: 0-1 min 80% A, 1-10 min linear gradient to 60% B, 10-11 min 60% B, 11-14 min linear gradient back to 80% A (initial conditions), 14-18 min 80% A (re-equilibration) (%, v/v). The flow rate was 15 ml/min. A Gilson (Villiers le Bel, France) pump model 321 with a liquidhandler model 215 was used, equipped with a UV detector (model UVNVIS-151) set at 276 nm. 800 μl of the crude N-lactoyl tyramine product was injected onto the system and a fraction was collected in the 8-10 min range. This run was repeated 10 times and combined fractions were evaporated to dryness under reduced pressure at 48° C. 0.1 g of 95%+pure N-lactoyl tyramine (measured by NMR) was obtained as a colorless oil.

Example 3

For a tasting session the following solutions were prepared:
1) A solution of 0.025% of a composition as prepared in example 1 in tap water;
2) A solution of 0.025% of a composition as prepared in example 1 and 0.3% NaCl in tap water;
3) A solution of 0.025% of a composition as prepared in example 1, 0.3% NaCl and 0.03% mono sodium glutamate in tap water;
4) A solution of 0.005% of a composition as prepared in example 2 in tap water;
5) A solution of 0.005% of a composition as prepared in example 2 and 0.3% NaCl in tap water; and
6) A solution of 0.005% of a composition as prepared in example 2, 0.3% NaCl and 0.03% mono sodium glutamate in tap water.

All samples were tasted by a professional panel. There was general agreement about the differences in taste between the samples.
Solutions 1) and 4) were described as having a clean mouthfeel, body and thickness. Solution 2) and 5) were described as having a longlasting effect, a clean mouthfeel, body and thickness and as bouillon-like.
Solution 3) and 6) were described as having a longlasting effect, a strong clean mouthfeel, body and thickness and as strong, natural and complex bouillon-like.

Example 4

Six samples were prepared:
1. Fish bouillon;
2. Fish bouillon+100 ppm of of a composition as prepared in example 1;
3. Nam Pla* ex Unilever Thailand;
4. Nam Pla ex Unilever Thailand+100 ppm of a composition as prepared in example 1;
5. Fish bouillon+20 ppm of a composition as prepared in example 2; and
6. Nam Pla ex Unilever Thailand+20 ppm of a composition as prepared in example 2.

Nam Pla is a Thai fish sauce produced from a mixture of fish (anchovy), salt and sugar that is fermented for more than 6 months at 30-35° C. Protein hydrolysate and lipid oxidation products are formed through microbiological and enzymatic breakdown of the fish.

All samples were tasted by a professional panel. There was general agreement about the differences in taste between the samples.

When sample 2 was compared with sample 1, it had more body and mouthfeel, a stronger sweet taste impression and a more longlasting effect.

When sample 4 was compared with sample 3, it had more body and mouthfeel, a stronger sweet taste impression and a more longlasting effect.

When sample 4 was compared with sample 3, it also had a more rounded, natural fermented fish character and was perceived as a higher quality Nam Pla.

When sample 5 was compared with sample 1, it had more body and mouthfeel, a stronger sweet taste impression and a more longlasting effect.

When sample 6 was compared with sample 3, it had more body and mouthfeel, a stronger sweet taste impression and a more longlasting effect.

When sample 4 and 6 were compared with sample 3, they also had a more rounded, natural fermented fish character and was perceived as a higher quality Nam Pla.

The invention claimed is:

1. Flavour composition comprising at least 0.1 wt. % of one or more flavouring substances and between 0.001 and 80 wt. % of a flavour modulating substance according to formula (I) and/or edible salts thereof:

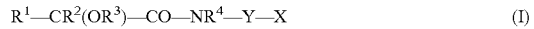

$$R^1\text{—}CR^2(OR^3)\text{—}CO\text{—}NR^4\text{—}Y\text{—}X \qquad (I)$$

wherein:
Y represents a covalent bond, $C_1$-$C_5$ alkylene or $C_{2-5}$ alkenyl, each optionally substituted with 1-5 substituents selected from hydroxyl, $C_1$-$C_3$ alkoxyl and $C_1$-$C_3$ acyl;
X represents phenyl, substituted with one or more substituents selected from hydroxyl, $C_1$-$C_3$ alkoxyl, and optionally further substituted with one or more substituents selected from $C_1$-$C_3$ hydroxyalkyl;
$R^1$ represents $C_2$-$C_6$ alkyl or $C_4$-$C_6$ cycloalkyl, wherein each carbon atom is substituted with a substituent selected from hydroxyl, oxo, carboxyl, $C_1$-$C_3$ alkoxyl, $C_1$-$C_3$ acyl;
$R^2$ represents hydrogen; $C_1$-$C_8$ alkyl, $C_2$-$C_8$ alkenyl, $C_3$-$C_8$ cycloalkyl, or $C_3$-$C_8$ cycloalkenyl, each optionally substituted with 1-8 substituents selected from hydroxyl, $C_1$-$C_3$ alkyl, $C_2$-$C_3$ alkenyl and $C_1$-$C_3$ carboxyl;
$R^3$ represents hydrogen; or $C_1$-$C_3$ acyl or $C_1$-$C_3$ alkyl, each optionally substituted with 1-3 hydroxyl groups; and
$R^4$ represents hydrogen; $C_1$-$C_6$ alkyl, $C_2$-$C_6$ alkenyl, $C_1$-$C_3$ acyl, $C_3$-$C_6$ cycloalkyl, $C_3$-$C_6$ cycloalkenyl or $C_1$-$C_6$ acyl, each optionally substituted with 1-6 substituents selected from hydroxyl, $C_1$-$C_3$ alkyl and $C_2$-$C_3$ alkenyl.

2. Flavour composition according to claim 1, wherein X represents hydroxyphenyl, optionally further substituted with one or two substituents selected from hydroxyl and methoxyl.

3. Flavour composition according to claim 1, wherein Y represents ethylene, optionally substituted with hydroxyl and/or methyl.

4. Flavour composition according to claim 3, wherein said flavour modulating substance is selected from N-lactoyl tyramine, N-gluconyl tyramine, N-lactoyl dopamine, edible salts thereof and mixtures thereof.

5. Flavour composition according to claim 1, wherein Y represents methylene, optionally further substituted with hydroxyl and/or methyl.

6. Flavour composition according to claim 5, wherein said flavour modulating substance is selected from N-lactoyl 4-hydroxybenzylamine, N-lactoyl vanillylamine and edible salts thereof.

7. Product selected from the group consisting of foodstuffs, beverages and pharmaceutics comprising at least 0.1 ppm of one or more flavour modulating substances according to formula (I) as defined in claim 1, and/or edible salts thereof.

8. Process of improving the flavour of a foodstuff, a beverage or a pharmaceutical product, comprising incorporating into said product one or more flavour modulating substances according to formula (1) as defined in claim 1, and/or edible salts thereof, in an amount of at least 0.1 ppm.

9. Flavour composition comprising at least 0.1 wt. % of one or more flavouring substances and between 0.001 and 80 wt. % of a flavour modulating substance according to formula (I) and/or edible salts thereof:

$$R^1-CR^2(OR^3)-CO-NR^4-Y-X \quad (I)$$

wherein:
Y represents ethylene, optionally substituted with hydroxyl and/or methyl;

X represents phenyl, substituted with one or more substituents selected from hydroxyl, $C_1$-$C_3$ alkoxyl, and optionally further substituted with one or more substituents selected from $C_1$-$C_3$ hydroxyalkyl;

$R^1$ represents hydrogen; $C_1$-$C_8$ alkyl, $C_2$-$C_8$ alkenyl, $C_3$-$C_8$ cycloalkyl or $C_3$-$C_8$ cycloalkenyl, each optionally substituted with 1-8 substituents selected from hydroxyl, oxo, $C_1$-$C_3$ alkyl, $C_2$-$C_3$ alkenyl, $C_1$-$C_3$ alkoxyl, $C_1$-$C_3$ acyl and $C_1$-$C_3$ carboxyl;

$R^2$ represents hydrogen; $C_1$-$C_8$ alkyl, $C_2$-$C_8$ alkenyl, $C_3$-$C_8$ cycloalkyl, or $C_3$-$C_8$ cycloalkenyl, each optionally substituted with 1-8 substituents selected from hydroxyl, $C_1$-$C_3$ alkyl, $C_2$-$C_3$ alkenyl and $C_1$-$C_3$ carboxyl;

$R^3$ represents hydrogen; or $C_1$-$C_3$ acyl or $C_1$-$C_3$ alkyl, each optionally substituted with 1-3 hydroxyl groups; and $R^4$ represents hydrogen; $C_1$-$C_6$ alkyl, $C_2$-$C_6$ alkenyl, $C_1$-$C_3$ acyl, $C_3$-$C_6$ cycloalkyl, $C_3$-$C_6$ cycloalkenyl or $C_1$-$C_6$ acyl, each optionally substituted with 1-6 substituents selected from hydroxyl, $C_1$-$C_3$ alkyl and $C_2$-$C_3$ alkenyl.

10. Flavour composition according to claim 9, wherein said flavour modulating substance is selected from N-lactoyl tyramine, N-gluconyl tyramine, N-lactoyl dopamine, edible salts thereof and mixtures thereof.

* * * * *